United States Patent
Kolata et al.

(10) Patent No.: US 6,592,514 B2
(45) Date of Patent: Jul. 15, 2003

(54) ORGAN RETRACTION TAPE POSITIONER AND METHOD FOR RETRACTING AND POSITIONING AN INTERNAL ORGAN

(75) Inventors: Ronald J. Kolata, Cincinnati, OH (US); Michael F. Clem, Maineville, OH (US); Christopher J. Hess, Lebanon, OH (US); Gary W. Knight, West Chester, OH (US); Kristin L. Jambor, Cincinnati, OH (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/855,997

(22) Filed: May 15, 2001

(65) Prior Publication Data

US 2002/0173701 A1 Nov. 21, 2002

(51) Int. Cl.[7] ................................................. A61B 1/32
(52) U.S. Cl. ......................... 600/37; 600/206; 600/210; 600/214; 600/231; 600/235
(58) Field of Search ................................. 600/201, 206, 600/210, 214, 227, 228, 231, 232, 233, 235, 37

(56) References Cited

U.S. PATENT DOCUMENTS

| | | | |
|---|---|---|---|
| 1,465,259 A | * | 8/1923 | Friedman |
| 2,863,444 A | * | 12/1958 | Winsten |
| 3,463,144 A | * | 8/1969 | Hammond |
| 3,983,863 A | | 10/1976 | Janke et al. |
| 4,973,300 A | | 11/1990 | Wright |
| 5,351,679 A | | 10/1994 | Mayzels et al. |
| 5,362,294 A | | 11/1994 | Seitzinger |
| 5,453,078 A | | 9/1995 | Valentine et al. |
| 5,509,890 A | | 4/1996 | Kazama |
| 5,947,896 A | | 9/1999 | Sherts et al. |
| 5,967,973 A | | 10/1999 | Sherts et al. |
| 6,015,382 A | | 1/2000 | Zwart et al. |
| 6,019,722 A | * | 2/2000 | Spence et al. ............. 600/210 |
| 6,102,853 A | | 8/2000 | Scirica et al. |

* cited by examiner

Primary Examiner—Jeffrey A. Smith
(74) Attorney, Agent, or Firm—Nutter McClennen & Fish, LLP

(57) ABSTRACT

A surgical retraction and positioning device comprises a stable platform and a flexible tape attached thereto for easier retraction and manipulation of a heart during cardiac surgery. The stable platform has an elongate body having a curved handle extending into an organ contacting base. The base is formed at the distal end of the handle and is at least partially concave to conform to the contours of the outer surface of the heart. A portion of a flexible element, such as umbilical tape, is secured to the base, leaving at least one free end to enable the surgeon to wrap, or secure, the heart against the organ contacting base.

21 Claims, 5 Drawing Sheets

ORGAN RETRACTION TAPE POSITIONER AND METHOD FOR RETRACTING AND POSITIONING AN INTERNAL ORGAN

CROSS-REFERENCE TO RELATED APPLICATIONS

Not applicable.

STATEMENT REGARDING FEDERALLY SPONSORED RESEARCH

Not Applicable.

FIELD OF THE INVENTION

The invention relates generally to surgical tools for displacing and positioning organs during surgery, and to methods pertaining thereto. More particularly, this invention relates to a device for retracting and supporting the heart during cardiac surgical procedures.

BACKGROUND OF THE INVENTION

Many patients with cardiac heart disease are often unable to treat their symptoms by dietary regulation or with drug treatments alone. One reason is that these non-invasive techniques may be inadequate to treat the severity of their condition. In some cases, there are no known drugs available that target the patient's specific needs. For these patients, invasive surgery remains the most effective treatment option.

Open heart surgeries are often employed to treat heart disease, and most often to reestablish blood supply to the heart muscle itself. The main purpose of most heart surgeries is to graft replacement vessels around blockages in what is commonly known as a coronary artery bypass graft (CABG) procedure. In certain situations, open heart surgery is required to either excise or replace a portion of the heart, such as in mitral valve repair or replacement.

All of these invasive surgical techniques require access to the heart. Typically, access is gained from a full sternotomy involving the forcible spreading apart of the sternal cavity, and entry into the pericardium. Other preferred ways of obtaining access include partial sternotomies, and thoracotomies, which involve minimal incisions and partial removal of the ribs to provide access to the underlying heart. Once inside the pericardium, the heart needs to be retracted and repositioned so that the surgeon can reach the target site where blockage or damage has occurred. Thus, manual manipulation and repositioning of the heart is usually necessary to reach the surgical site.

In coronary bypass operations, for example, graft vessels can be anastomosed to the anterior descending artery, the circumflex artery and the posterior descending artery. Whereas the anterior descending artery lies on the front surface of the heart and is easily accessible to the surgeon, the circumflex and posterior descending arteries lie on the back surface of the heart and are reached only with additional help from assistants or devices. Thus, bypass operations are especially difficult because of the inaccessibility of the field of operation on the lateral and posterior sides of the heart.

Several methods have conventionally been used to achieve the required exposure. Ordinarily a surgical assistant is employed to manually lift and rotate the heart. This scenario can poses several problems. The assistant's hand can get in the way of the operative field, and the assistant, who often stands adjacent to the surgeon, may restrict the surgeon's movements. It is also difficult to keep the heart in a steady position. This form of manual manipulation is not only cumbersome but extremely tiring for both the assistant and the surgeon. In addition, manually handling the heart can cause bruising of the muscle and damage to the surrounding tissue.

Currently available manipulators and retractors for positioning either a stopped or beating heart to facilitate surgical access suffer from several drawbacks. Tools such as inflatable cushions and gauze pads that are used to shim organs into position present problems such as the risk that the tools will inadvertently be left behind after the procedure is complete, risk of damage to the surface of the heart or pericardium during their placement and removal, and lack of ability to control and readjust organ elevation and position. Furthermore, these inflatable cushions, or balloons, and gauze pads are difficult to place and remove when using minimal incisions. Other available tools include rigid manipulators with sharp contact points that can cause tissue trauma during intricate surgical movements.

Presently, a common method of manipulating the heart involves using simple strands or loops of umbilical tape placed in various positions around the heart to facilitate repositioning. However, these tapes are floppy and lack structure or foundation for subsequent manipulation. Another conventional method requires placing sutures through the pericardial tissue and then pulling on the suture strands to gain access to the lateral and posterior sides of the heart. But such a method renders possible tearing or damaging the pericardial tissue as the suture strands are tugged and pulled.

The heart muscle and its surrounding membrane are delicate tissues. Any trauma to this surface, or to the heart itself, can subsequently cause adhesions to form, and therefore any means of manipulation or retraction must be very gentle. There is presently an unfulfilled need for devices that will permit atraumatic manipulation and stabilization of a beating or stopped heart or organ to facilitate exposure of all surfaces of the heart or organ during surgery, so the surgeon can effect organ manipulation and positioning from outside the surgical cavity in a simplified and standardized manner.

SUMMARY OF THE INVENTION

The present invention overcomes the drawbacks inherent in prior art surgical methods and devices by providing a stable platform for retraction tape positioning of a beating or stopped heart during cardiac surgery, thus allowing for more consistent placement and easier retraction. In efforts to expose the various posterior and lateral surfaces of the heart during a thoracotomy or sternotomy, the present device allows the surgeon to place soft fabric tapes having an anchoring point around the apex of the heart and/or through the transverse sinus. Placing the stable platform underneath the heart provides the surgeon with a posterior pivot point with which he can gain access to the posterior and lateral regions. By simply applying tension to the tape, the surgeon is able to access these regions in a safe and efficient manner.

In one embodiment of the present invention, the surgical retraction and positioning device comprises a stable platform and a flexible tape attached thereto. The stable platform has an elongate body having a curved handle extending into an organ contacting base. The base is formed at the distal end of the handle and is at least partially concave to conform to the contours of the outer surface of the heart. A portion of a flexible element, such as umbilical tape, is secured to the base, leaving at least one free end for the surgeon to wrap, or secure, the heart against the organ contacting base.

In another embodiment, the organ contacting base also includes at least one laterally extending lobe. However, the organ contacting base can also include two laterally extending lobes, with each lobe extending in opposite, or different directions. The lobes can be concavely curved such that the organ contacting base cradles the heart. In another aspect of the present invention, one of the laterally extending lobes can be longer than the other lobe. The different designs of the organ contacting base provide the surgeon with the ability to support the heart in various positions while preventing blockage of specific target areas on the underside of the heart muscle.

The elongate body, or stable platform, can be formed of either a rigid or semi-rigid biocompatible material. Suitable materials include injection-molded plastics, shape-memory polymers, polymer composites, malleable metals, shape-memory metals, and metal alloys. The body can also be integrally formed. The handle can be at least partially convex, or have an S-shaped curve. The proximal end of the handle is adapted to be manually held, or secured to an external surgical retractor.

The flexible element attached to the organ contacting base can be either umbilical tape, or surgical grade fabric, ribbon, or cord. The flexible element must be able to conform to the outer surface of the heart when passed beneath or around the apex of the heart to secure the organ to the base. The end of the flexible element, along with the handle of the device, allows the surgeon to manipulate the heart's position and orientation during surgery.

Although the invention is described mainly in terms of cardiac surgical techniques and the need for atraumatic positioning and manipulation devices, it is clear that need for such devices also exists in surgical procedures in other anatomic locations. For example, procedures that require lifting or positioning of solid organs including the liver and the spleen would be enhanced by the present invention.

Further features of the invention, its nature and various advantages, will be more apparent from the accompanying drawings and the following detailed description of the drawings and the preferred embodiments.

DETAILED DESCRIPTION OF THE INVENTION

Figure 1:
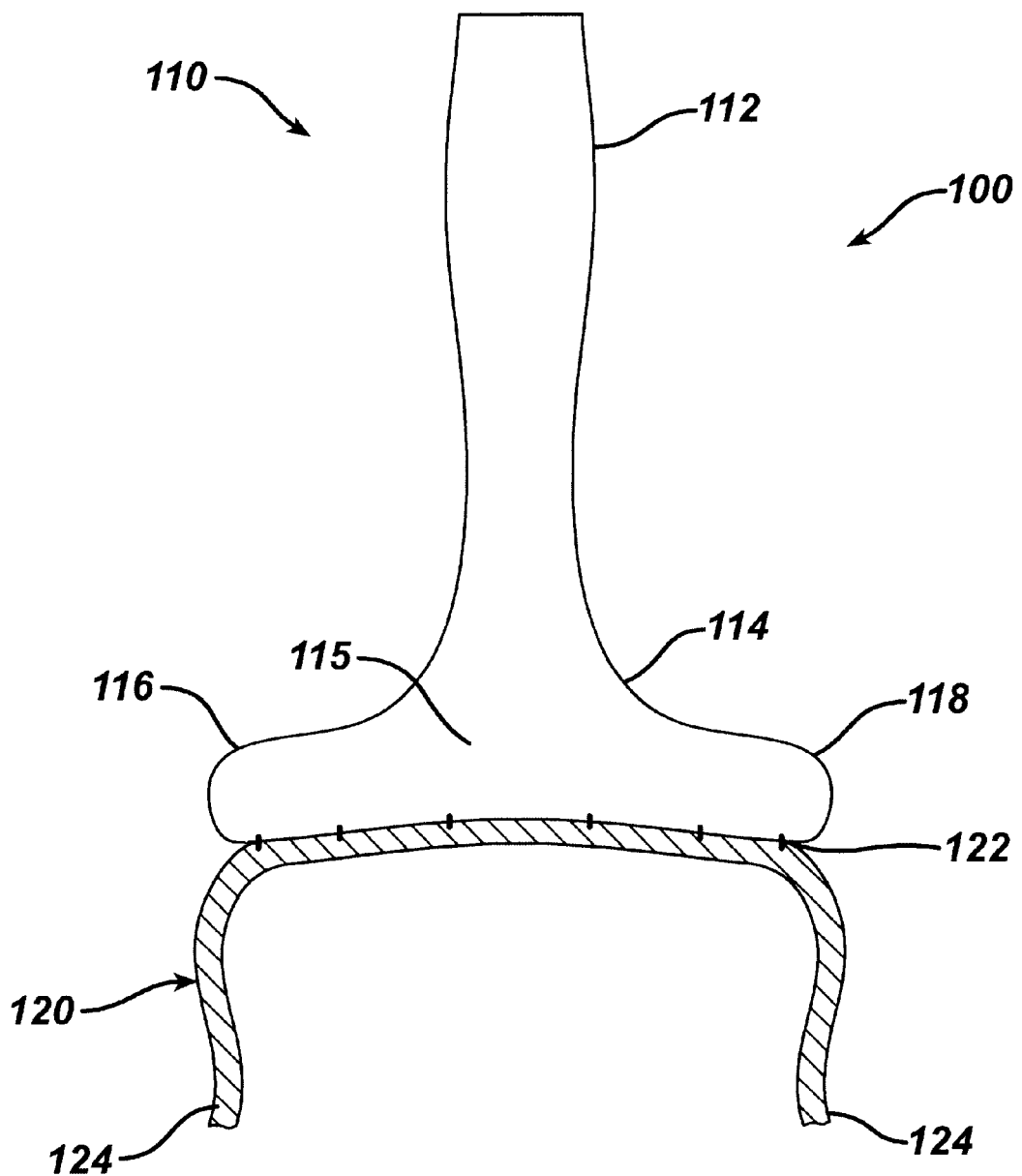
FIG. 1 is a planar view of a retraction and positioning device of the present invention.
Figure 2:
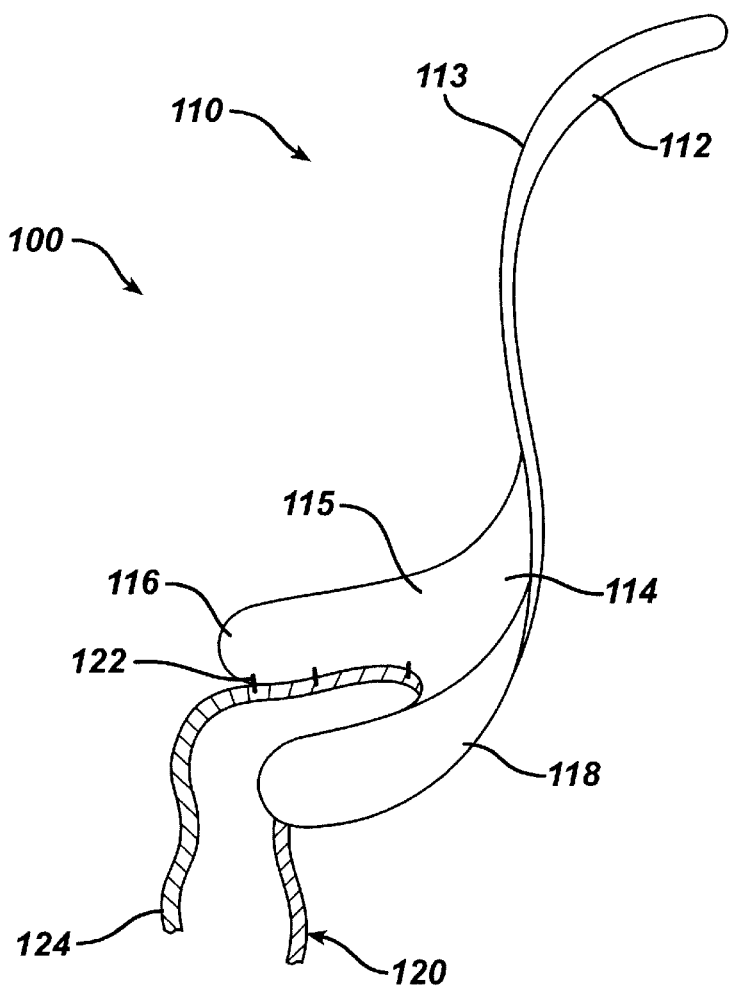
FIG. 2 is a side-view of the device of FIG. 1.

Referring now to the drawings and particularly to FIG. 1, retraction and positioning device 100 includes an elongate body 110 having a handle 112 and an organ contacting base 114. As shown in FIG. 2, handle 112 is curved and extends into base 114. The base 114 is formed at the distal end of the handle 112 and has an organ contacting surface 115 along its inner surface that is at least partially concave to conform to the contours of the outer surface of the heart. Handle 112 is also curved, being at least partially convex, or S-shaped along its inner surface, i.e., the surface facing the organ. Collectively, the handle 112 and organ contacting base 114 form a stable platform on which the heart or organ can be gently secured for manipulation and retraction during surgery.

In one embodiment, the organ contacting base 114 also includes at least one or more laterally extending lobes. FIGS. 1 and 2 illustrate an organ contacting base 114 that includes first and second laterally extending lobes 116, 118, each of which extends in a different direction away from the base 114. As depicted in FIG. 2, the lobes 116, 118 can be concavely curved along their inner surface, i.e., the surface facing the organ, such that the heart can be cradled within the organ contacting base 114.

Figure 3:
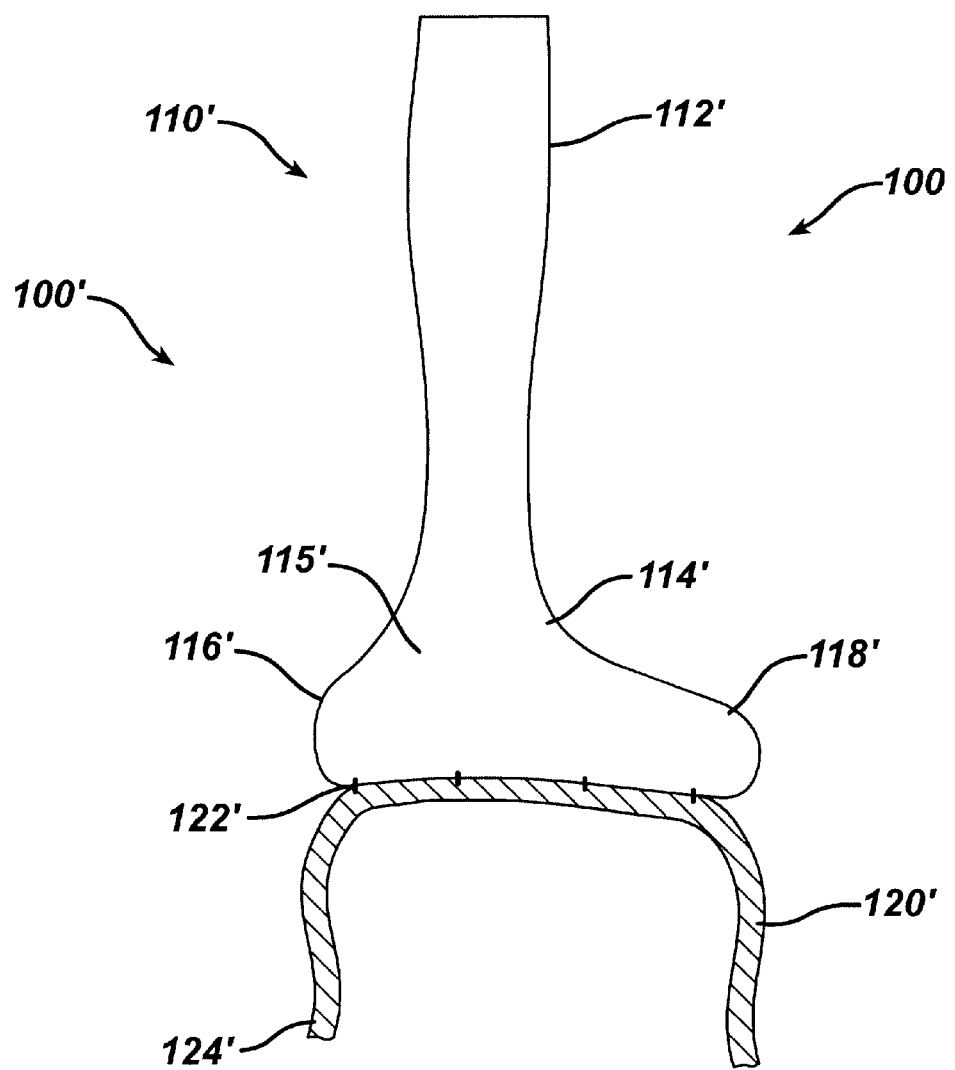
FIG. 3 is a planar view of another embodiment of the device of the present invention.

FIG. 3 shows an alternative embodiment wherein device 100' has a first laterally extending lobe 118' that is longer than a second laterally extending lobe 116'. In all other respects, device 100' is similar to device 100 of FIGS. 1 and 2, with similar elements being designated with the symbol "'" following the element number. Asymmetric device 100' provides a stable platform 110' for the heart that is side-specific, allowing unencumbered access to either the right or left underside of the heart. It is contemplated that the device 100, 100' of the present invention can also be made in various sizes, with either a left 116' or right lobe 118' that is longer than the other. By providing the surgeon with different sizes and side-specific designs for the retraction and positioning device 100, 100', the surgeon can provide customized retraction and positioning of the heart. Depending on which side the blockage or target site is on the heart, the proper device 100, 100' can be utilized without impeding the surgical field.

To effect securement of the heart muscle against the organ contacting base 114, a flexible element 120 such as umbilical tape is attached at least along a portion thereof to a portion of the organ contacting base 114, as shown in FIGS. 1–4. The free ends 124 of the flexible element 120 can wrap around the apex of the heart and/or through the transverse sinus to secure the heart against the base 114. Surgical sutures 122 can be used to attach the flexible element 120 to the organ contacting base 114.

Figure 4:
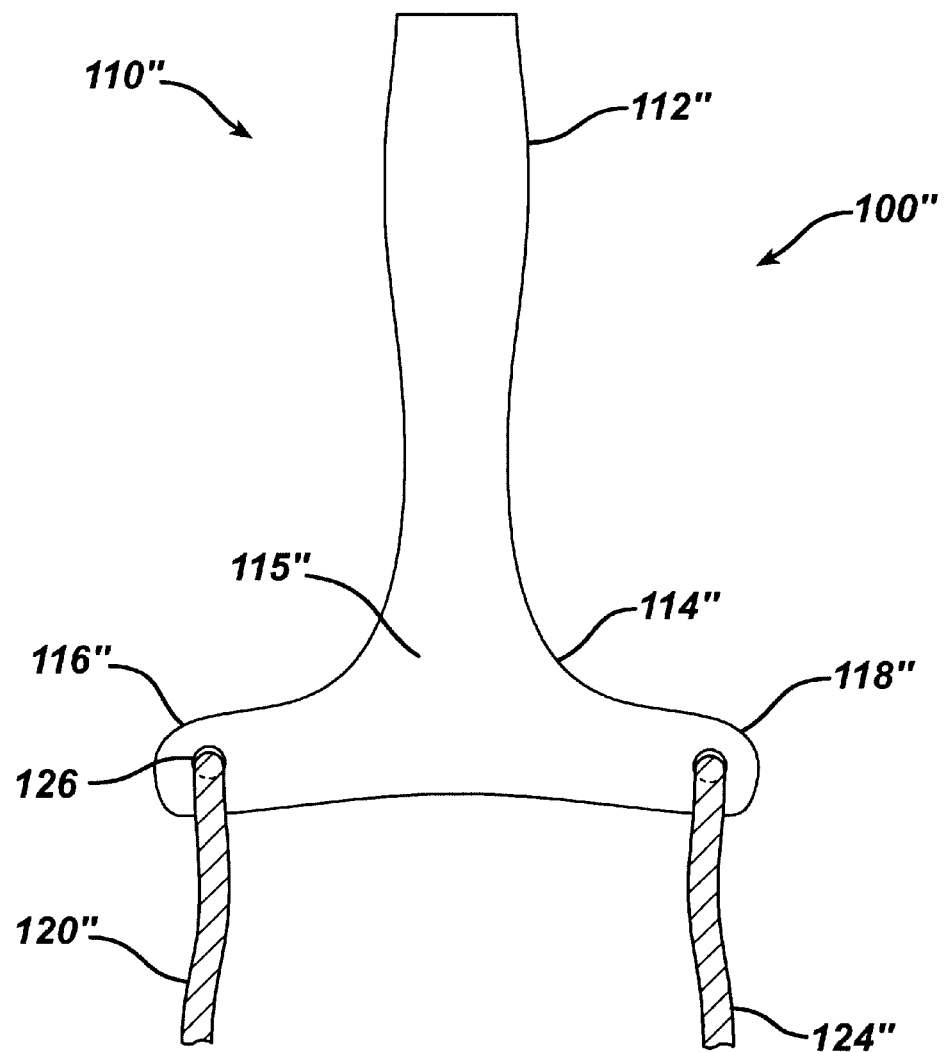
FIG. 4 is a planar view of yet another embodiment of the device of the present invention.

FIG. 4 illustrates another method of attaching flexible element 120" to the organ contacting base 114". In this particular embodiment, device 110" includes an organ contacting base 114" having lobes 116" and 118", each with a hole 126 through which a flexible element 120" may be threaded and secured. While device 100" is depicted with two lobes 116" and 118" of equal length, it is contemplated that either lobe 116" or 118" can be manufactured with differing lengths. In all other respects, device 100" is similar to device 100 of FIGS. 1 and 2, with similar elements being designated with the symbol """ following the element number.

The elongate body 110, or stable platform, which includes the handle 112 and organ contacting base 114, can be integrally formed of either a rigid or semi-rigid biocompatible material. For example, elongate body 110 can be formed of injection-molded plastic, shape-memory polymer, or polymer composite. Alternatively, elongate body 110 can comprise a malleable metal, shape-memory metal, or metal alloy. Suitable biocompatible materials include titanium, titanium alloys and Nitinol. Where device 100 is formed of a malleable material, the surgeon can adjust the curvature of the lobes 116, 118 to achieve a better fit with the heart or organ, and maneuver the handle to the proper position as needed during surgery. Additionally, an asymmetric device 100 formed of malleable material lets the surgeon easily adjust the curvature of the elongate body 110 to create a side-specific organ contacting base 114.

Figure 5:
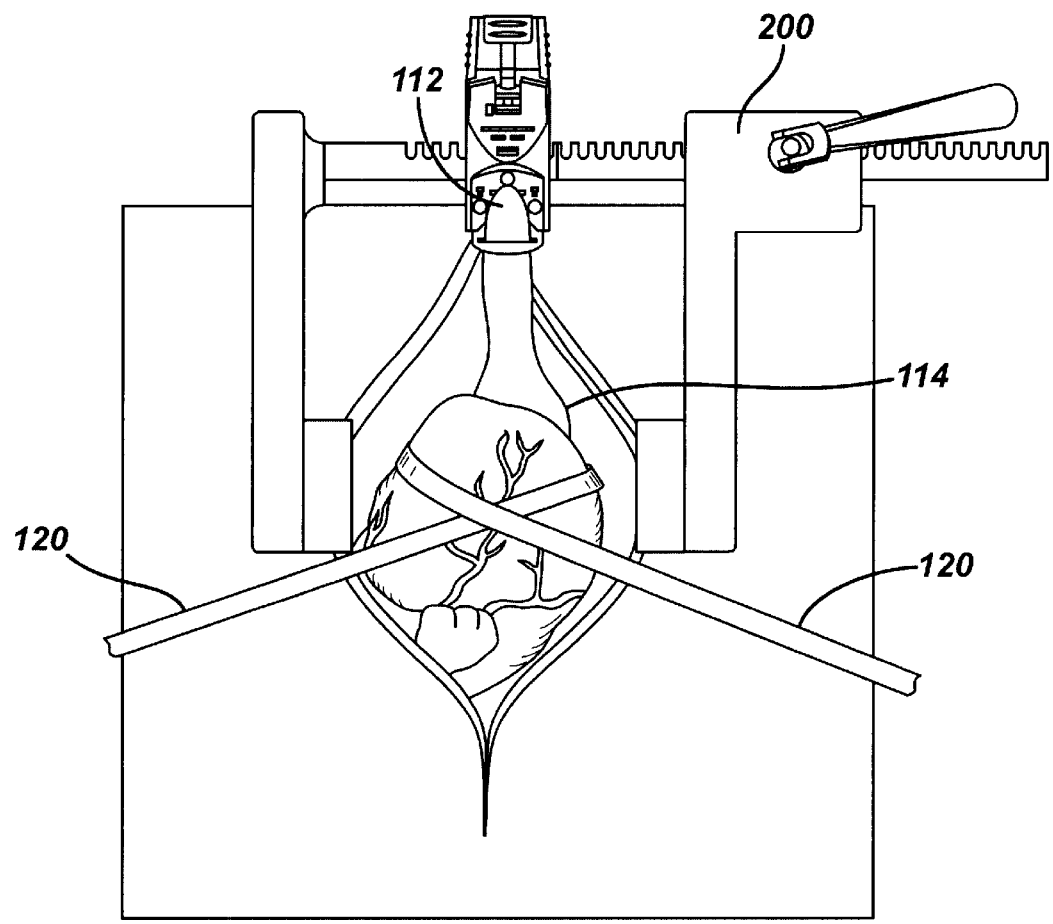
FIG. 5 is a perspective view of the device of FIG. 1 in use with a surgical retractor.

Handle 112 is adapted to be grasped manually or connected to an external surgical retractor 200, as shown in FIG. 5. In the preferred embodiment shown, proximal end of handle 112 is adapted to attach to the retractor 200. Handle 112, therefore, needs to be of sufficient length and size to properly connect to the surgical retractor 200. Preferably, the elongate body 110 is about 6 to 8 inches long, and 2 to 3 inches wide.

Flexible element 120 should be constructed such that it is able to conform to the outer surface of the heart when passed beneath or around the apex of the heart to secure the organ to the base 114. Suitable materials for the flexible element 120 include wide umbilical tape, or similar soft fabric materials such as surgical grade fabric, ribbon, or cord. The ends of the flexible element 120 may be secured in any known manner in the art, such as by tying, to keep the fabric from fraying.

In use, as illustrated in FIG. 5, device 100 is positioned such that the bottom of the Y-shaped, or fluked, elongate body 110 lies under the heart, between the heart and the pericardium. The top of the elongate body 110, i.e., the handle 112, is clamped onto external retractor 200. Flexible elements 120 are passed around the heart, and the free ends 124 extend out of the surgical cavity. Elongate body 110 provides an anchor for the flexible elements 120 so that the surgeon can pull on the flexible elements 120 to manipulate the position of the heart and obtain access to its target portions.

Although the invention is described mainly in terms of atraumatic positioning and manipulation devices for cardiac surgical techniques, it is clear that need for such devices also exists in surgical procedures in other anatomic locations. For example, procedures that require lifting or positioning of solid organs including the liver and the spleen would be enhanced by the present invention.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A surgical device for retracting and positioning an internal organ during a surgical procedure, comprising:
    a monolithic elongate body having at a proximal end a curved handle and an organ contacting base formed at a distal end thereof, the organ contacting base having at least a partially concave organ contacting surface;
    at least one flexible element having a portion thereof secured to the organ contacting base, the at least one flexible element including at least one free end and being conformable to an outer surface of an organ placed against the organ contacting base.

2. The device of claim 1, wherein the organ contacting base comprises at least one laterally extending lobe.

3. The device of claim 2, wherein the organ contacting base comprises first and second laterally extending lobes, the lobes extending in different directions.

4. The device of claim 3, wherein the first and second lobes are of unequal length.

5. The device of claim 3, wherein each of the first and second laterally extending lobes has an inner surface that is concavely curved.

6. The device of claim 2, wherein the at least one laterally extending lobe has an inner surface that is concavely curved.

7. The device of claim 1, wherein an inner surface of the handle is at least partially convex.

8. The device of claim 1, wherein the flexible element is selected from the group consisting of umbilical tape, surgical grade fabric, ribbon, and cord.

9. The device of claim 1, wherein the flexible element is attached to the organ contacting base with surgical sutures.

10. The device of claim 1, wherein the handle is adapted to connect to a surgical retractor.

11. The device of claim 1, wherein the elongate body is formed of rigid or semi-rigid material.

12. The device of claim 1, wherein the elongate body is formed from injection-molded plastic.

13. The device of claim 1, wherein the body is formed from a material selected from the group consisting of a metal, a metal alloy, a polymer, and a composite.

14. The device of claim 13, wherein the body is formed of titanium or Nitinol.

15. The device of claim 1, wherein the elongate body is about 6 to 8 inches long.

16. The device of claim 1, wherein the elongate body is about 2 to 3 inches wide.

17. A surgical device for retracting and positioning an internal organ during a surgical procedure, comprising:
    a monolithic elongate body having at a proximal end a convexly curved handle and an organ contacting base formed at a distal end thereof, the organ contacting base having at least a partially concave organ contacting surface, the organ contacting base further including at least one laterally extending lobe; and
    at least one flexible element having a portion thereof secured to the organ contacting base, the at least one flexible element including at least one free end and being conformable to an outer surface of an organ placed against the organ contacting base.

18. Method for retracting and positioning an internal organ during a surgical procedure, comprising the steps of:
    providing a surgical device comprising a monolithic elongate body having at a proximal end a curved handle and an organ contacting base formed at a distal end thereof, the organ contacting base having at least a partially concave organ contacting surface, and at least one flexible element having a portion thereof secured to the organ contacting base, the at least one flexible element including at least one free end and being conformable to an outer surface of an organ placed against the organ contacting base;
    placing the surgical device against and in supportive relation to the organ; wrapping the free end of the at least one flexible element around the organ to secure the organ against the surgical device; and manipulating the handle and free end of the at least one flexible element to retract and position the organ.

19. The method of claim 18, wherein the step of manipulating the handle includes attaching the handle to a surgical retractor and retracting the surgical device.

20. The method of claim 18, wherein the step of manipulating the handle includes manually gripping and maneuvering the handle.

21. The method of claim 18, further including the step of accessing and performing the surgical procedure on an underside of the organ.

* * * * *